US012690840B2

(12) United States Patent
Munding

(10) Patent No.: US 12,690,840 B2
(45) Date of Patent: Jul. 28, 2026

(54) ULTRASOUND PATCH WITH INTEGRATED FLEXIBLE TRANSDUCER ASSEMBLY

(71) Applicant: 1929803 Ontario Corp., Sudbury (CA)

(72) Inventor: Chelsea Munding, Sudbury (CA)

(73) Assignee: 1929803 Ontario Corp., Sudbury (CA)

( * ) Notice: Subject to any disclaimer, the term of this patent is extended or adjusted under 35 U.S.C. 154(b) by 0 days.

(21) Appl. No.: 18/942,227

(22) Filed: Nov. 8, 2024

(65) Prior Publication Data

US 2025/0152132 A1     May 15, 2025

Related U.S. Application Data

(60) Provisional application No. 63/598,052, filed on Nov. 10, 2023.

(51) Int. Cl.
| | |
|---|---|
| *A61B 8/00* | (2006.01) |
| *A61B 8/06* | (2006.01) |
| *B06B 1/06* | (2006.01) |
| *G01S 7/52* | (2006.01) |
| *G01S 15/89* | (2006.01) |

(52) U.S. Cl.
CPC .............. *A61B 8/4236* (2013.01); *A61B 8/06* (2013.01); *B06B 1/0622* (2013.01); *G01S 7/52079* (2013.01); *G01S 15/8913* (2013.01); *B06B 2201/76* (2013.01)

(58) Field of Classification Search
CPC ....... A61B 8/4236; A61B 8/06; B06B 1/0622; B06B 2201/76; G01S 7/52079; G01S 15/8913
See application file for complete search history.

(56) References Cited

U.S. PATENT DOCUMENTS

| | | | | |
|---|---|---|---|---|
| 11,937,976 | B2 * | 3/2024 | Eibl ..................... | A61B 8/4494 |
| 11,980,476 | B1 * | 5/2024 | Wybo ................. | A61B 5/4519 |
| 2020/0022670 | A1 * | 1/2020 | Eibl ......................... | A61B 8/56 |
| 2021/0212658 | A1 * | 7/2021 | McGrath ............... | A61B 8/466 |
| 2022/0000447 | A1 * | 1/2022 | Eibl ..................... | A61B 8/4494 |
| 2023/0414299 | A1 * | 12/2023 | Khuri-Yakub ....... | A61B 8/4494 |
| 2024/0389976 | A1 * | 11/2024 | Gold .................... | A61B 8/4281 |

* cited by examiner

*Primary Examiner* — Dixomara Vargas
(74) *Attorney, Agent, or Firm* — Perkins Coie LLP

(57)     ABSTRACT

A self-contained ultrasound patch assembly for detecting fluid flow in a vessel includes piezo elements that can transmit ultrasonic energy and detect echo signals. A flex module has two support portions connected to respective ones of the elements with a hinged portion coupled to the support portions, allowing them to be positioned angularly relative to each other. Electronics that direct the elements to transmit ultrasonic energy and process detected echo signals are in communication with the elements through the flex module. A transducer frame includes a plurality of crush points to retain the flex module in an aligned position. The frame supports the elements at a fixed angular position with respect to each other. A housing encloses the electronics and frame, and fixedly retains the frame to position the elements to transmit toward a flat bottom surface and away from a top surface of the housing.

20 Claims, 11 Drawing Sheets

ULTRASOUND PATCH WITH INTEGRATED FLEXIBLE TRANSDUCER ASSEMBLY

CROSS-REFERENCE TO RELATED APPLICATIONS

This application claims the benefit of and priority to U.S. Provisional Patent Application No. 63/598,052, titled ULTRASOUND PATCH WITH INTEGRATED FLEXIBLE TRANSDUCER ASSEMBLY, filed Nov. 10, 2023, which is incorporated herein by reference.

TECHNICAL FIELD

The disclosed technology relates to ultrasound devices designed to detect fluid flow in a vessel.

BACKGROUND

Conventional medical ultrasound devices are typically heavily dependent on the operator's skill and experience to provide high quality and accurate ultrasound images. The positioning of the transducer, angle of incidence, and pressure applied can greatly affect the clarity and interpretation of the images. This places a significant burden on the operator to have the necessary expertise and training to obtain reliable results. In many clinical and diagnostic settings, physicians or other medical personnel often use ultrasound devices to assess how well blood is flowing through a subject's vasculature. Many ultrasound devices require that an operator use one hand to hold an ultrasound transducer at a particular angle to a vessel while using the other hand to control a base unit of the ultrasound imaging system, thereby preventing the performance of other tasks while measuring flow. Other ultrasound transducer devices can be affixed to a subject to continuously or periodically measure flow in a vessel, thereby freeing up the hands of the caregiver. An example of an ultrasound patch for detecting and measuring fluid flow in a vessel that provided a significant advancement is described in U.S. Patent Application Publication No. 2020/0022670, titled Ultrasound Patch for Detecting Fluid Flow, which is incorporated herein in its entirety by reference thereto. The disclosed technology relates to improvements in the design of the ultrasound transducer devices that can be affixed to a subject. There is a need for improved ultrasound systems for detecting blood or other fluid flow in a patient.

Figure 1A:
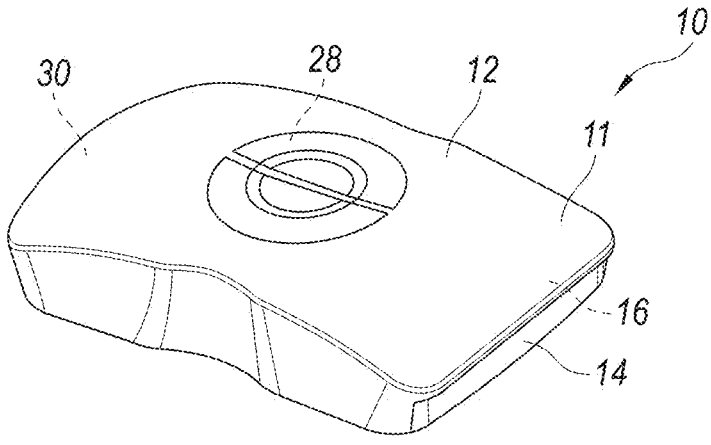
FIG. 1A is a top isometric view of an ultrasound patch assembly in accordance with aspects of the present technology.

The assemblies, structures, components, and techniques introduced herein may be better understood by referring to the following Detailed Description in conjunction with the accompanying drawings, in which like reference numerals indicate identical or functionally similar elements. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

The disclosed technology relates to an improved ultrasound patch assembly that overcomes drawbacks in the prior art and provides other advantages. Embodiments of the present technology provide an ultrasound patch assembly with a frame-mounted flexible transducer assembly configured to detect flow in a vessel (e.g., artery, vein, etc.). The ultrasound patch assembly includes the electronics, power source (e.g., battery), circuit board(s), memories, antenna, speaker, etc., within a housing to form a self-contained unit that transmits ultrasound waves, detects ultrasound echoes, processes data, and communicates wirelessly and/or through a cable with one or more other devices. As will be discussed in detail below, embodiments of the ultrasound patch assembly include air-backed piezoelectric elements ("piezo elements") that produce ultrasonic waves (e.g., ultrasonic energy) for delivery towards a vessel, and produce electronic signals from the corresponding reflected and received acoustic echo signals. In some embodiments, the base or patient-interfacing side of the patch assembly has a flat bottom positionable on the skin of a patient adjacent to selected vessels to position the transducer piezo elements within the housing as close as possible to the vessels (e.g., carotid and/or jugular vessels) to acquire ultrasonic data associated with the flow through the vessels. The patient-interfacing side of the patch can have other shapes and be configured to image flow in other anatomy.

In some embodiments, the ultrasound patch assembly has the flexible transducer assembly with two or more piezo-electric (piezo) elements supported on a sturdy flex module mountable on a frame to hold the piezo elements in selected positions within the housing for transmitting ultrasonic energy and detecting echo signals from the flow through the vessels. The flex module has first and second support portions that each connect to a respective one of the piezo elements, and the support portions are interconnected by a hinged portion configured to allow the support portions and associated piezo elements to be positioned angularly relative to each other.

The ultrasound patch assembly has electronics fully contained within the housing operatively coupled to the two piezo elements through the flex. The electronics are configured to direct the two piezo elements to transmit the ultrasonic energy as well as to process the detected echo signals. The ultrasound patch assembly has transducer support members formed within the housing and configured to receive and retain the flexible transducer assembly so the flex module and associated piezo elements are fixedly retained within the housing at the selected angular orientation relative to each other. A transducer frame in the housing positions the flexible transducer assembly on the support members during assembly for secure, accurate positioning of the transducer elements in the housing. The frame can have an alignment portion that engages a mating alignment portion on the flexible transducer assembly to fixedly retain the flex module and piezo elements in an aligned position on the transducer frame within the housing. The arrangement of the support elements and the transducer frame defines the positioning of the two piezo elements relative to the patient-interfacing side of the patch assembly.

The housing encloses the electronics and the transducer frame within an interior area. The housing includes a top surface opposite a bottom surface that defines the patient-interfacing side of the patch assembly. During use with the patient, the top surface faces away from the skin of the patient and the bottom surface faces toward the skin of the patient. The housing fixedly retains the transducer frame and the flex module to position the two piezo elements to transmit the ultrasonic energy toward the bottom surface and away from the top surface.

In other embodiments, the ultrasound patch assembly configured for use on the skin of a patient to detect fluid flow in a vessel in the patient includes a flexible transducer assembly with piezo elements that have front and rear surfaces and that are configured to transmit ultrasonic energy and detect echo signals. The flexible transducer assembly has a flex module with support portions connected to piezo elements. The flex module also has electrodes with conductive material. The support portions and the hinged portion are configured to allow the first and second support portions and associated piezo elements to be positioned angularly relative to each other. Electrodes are positioned on the first and second support portions. The conductive material electrically interconnects the rear surfaces of associated ones of the piezo elements and the electrodes. An air gap is formed between portions of the piezo elements and electrode-free portions of the first and second support portions. A base of the ultrasound patch assembly has angled support members that support the piezo elements in a predetermined angular orientation. The piezo elements are sandwiched between the support elements and a transducer frame, which includes first and second surfaces that receive the first and second support portions of the flex module. The first and second surfaces have an angular arrangement to position the piezo elements against the angled support members. One or more retention elements engage at least one of the piezo elements to retain the first and second support portions of the flex module relative to the first and second surfaces of the transducer frame.

In still further embodiments, an ultrasound patch assembly is configured for use on the skin of a patient to detect fluid flow in a vessel in the patient. The ultrasound patch transducer includes first and second piezo elements configured to transmit ultrasonic energy and detect echo signals, and each have front and rear surfaces. The piezo elements are mounted on angled support members, wherein the piezo elements are sandwiched between the support members and a transducer frame enclosed within a housing. The transducer frame is made of a rigid material and has first and second surfaces facing the piezo elements. Sidewalls extend outwardly from opposite ends of the first and second surfaces. The sidewalls and first and second surfaces form a receiving area for the first and second piezo elements. The first and second surfaces have an angular arrangement to position the front surfaces of the first and second piezo elements securely against the angled support elements of the base at less than 180 degrees with respect to each other. At least one of the sidewalls includes a retention feature protruding from the sidewall into the receiving area proximate the front surface of at least one of the first and second piezo elements. The housing includes a top surface that faces away from the skin of the patient and a bottom surface opposite the top surface that faces toward the skin of the patient during use with the patient. The housing retains the transducer frame at a fixed position to position the first and second piezo elements to transmit the ultrasonic energy toward the bottom surface and away from the top surface.

A method of manufacturing and/or assembling the self-contained ultrasound patch assembly is also disclosed herein. The manufacturing/assembly process also includes the necessary installation and interconnection of elements discussed previously, such as electronics, power source (e.g., battery), circuit board(s), memories, antenna, speaker, etc., within the same housing as the piezo elements to form a self-contained unit that transmits ultrasound waves, detects ultrasound echoes, processes data, and communicates wirelessly and/or through a cable with one or more other devices and/or networks. The ultrasound patch assembly can include a flexible transducer assembly that has a flexible printed circuit board layer securely connected to the piezo elements with a non-conductive epoxy. The epoxy interfaces with at least substantially inactive areas of the elements and aids in bonding. Two separate piezo elements are fixed to support members formed in the assembly's housing, so as to position the piezo elements angularly with respect to each other and relative to the bottom surface of the housing that faces the patient when in use.

During assembly, the flexible transducer assembly is connected to a selected one of a plurality of transducer frames, and the frame is snapped into a base of the ultrasound patch assembly to fixedly position each of the piezo elements on a respective one of the angled support members of the base. The piezo elements can be bonded or otherwise permanently affixed to the angled support members as the transducer frame holds the piezo elements against the support members. The components of the ultrasound patch assembly can be fully assembled inside the base, allowing all parts to be fit together in a systematic and reproducible fashion. The top shell can be attached to the base to provide a secure unit that may be waterproof.

Each of the plurality of transducer frames have a commonly shaped receiving area that receives and retains the flex module and piezo elements, although each frame can be configured to fixedly support and hold the piezo elements at different angular orientations to substantially match the angles of the support members in a selected base for the ultrasound patch assembly. The angular orientation of the support members can be less than 180 degrees such that the ultrasound beams intersect and focus at different imaging depths. In other embodiments, the angular orientation can be 180 degrees or more to direct ultrasound beams and detect echo signals from ultrasound beams that do not intersect. In some embodiments, the plurality of transducer frames can have sacrificial crush points on the first and second surfaces. These sacrificial crush points can absorb great force until the piezo elements become flat and maintain alignment of the piezo elements against the angled support members. In additional embodiments, one or more lenses can be used to change the transmission and/or detection to an angle that is non-normal to a front surface of the piezo element(s).

Additionally, several methods are disclosed for acoustically potting the piezo elements in the base. A non-conductive epoxy or other potting material with the desired acoustic properties can be used. The transducer frame and piezo elements can be secured in the base either before or after the potting material is placed in the base. The frame and element configuration provide opening(s) for air bubbles to escape so that the bubbles do not become trapped in the potting material between the elements and the inner surface of the base.

In other embodiments, multiple individual piezo elements in two or more different arrays can be used instead of the two separate piezo elements. Two arrays of elements can be attached to the stiffened flex module with the non-conductive epoxy. The two arrays can be held at an angle with respect to each other in the transducer frame and installed in the same patch assembly housing. In some cases, the stiffened flex module can be flexed or bent to form a curvilinear shaped transducer face to increase the imaging area. In some cases, the ultrasonic information associated with each of the elements in the arrays of elements can be evaluated to identify the elements that are seeing flow. Elements that are imaging tissue and not seeing flow can be turned off, saving power and reducing signal-to-noise ratio (SNR). In some cases, multiple vessels can be imaged simultaneously, and multiple imaging areas may be defined.

Figure 1B:
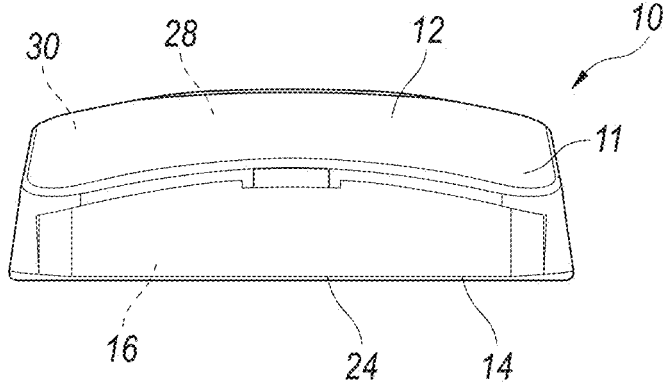
FIG. 1B is a side elevation view of the ultrasound patch assembly of FIG. 1A.
Figure 1C:
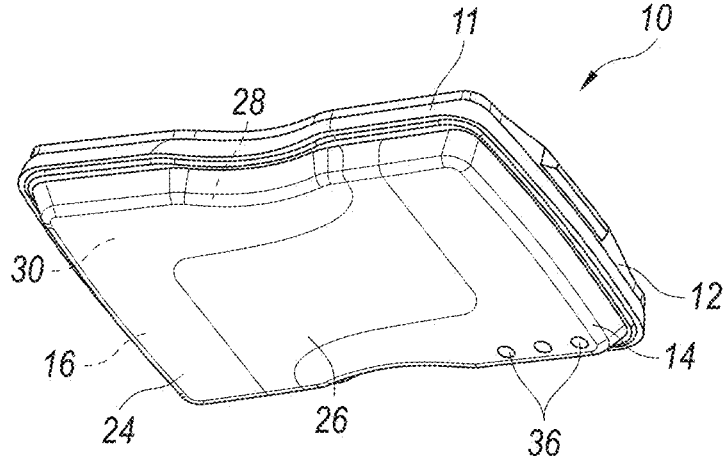
FIG. 1C is a bottom isometric view of the ultrasound patch assembly of FIG. 1A.

FIG. 1A-1C shows an ultrasound patch assembly 10 in accordance with embodiments of the present technology. The ultrasound patch assembly 10 can be a small, self-contained unit that can interface directly with the skin of a patient, with the use of ultrasonic gel or other acoustic coupling medium therebetween, to detect fluid flow in a vessel, such as blood flow in an artery or vein. The housing 11 of the patch assembly 10 includes top and base portions 12 and 14 that define an interior area 16 configured to contain a flexible transducer assembly 20 with one or more pairs of transducer 38 piezo elements 22 (FIG. 1D), which direct ultrasound energy (e.g., ultrasound waves) into a subject and receive echo signals from moving blood or other body fluids. In some embodiments, the top and base portions 12 and 14 (FIG. 1A) can be sealably interconnected to create a hermetic seal and allow the ultrasound patch assembly 10 to be submersible in cleaning agents, as well as preventing tampering with the patch assembly 10.

The base 14 of the housing 11 has a bottom surface 24 that defines a flat skin-contacting portion 26 of the patch assembly 10. The housing 11 of some embodiments can be sized so the bottom surface 24 can be positioned adjacent to the area between the patient's sternocleidomastoid muscle and the trachea, so as to be close to the patient's carotid artery and the jugular vein. As discussed further below, the piezo elements 22 are held within the housing 11 adjacent to the bottom surface 24 and transmit/receive ultrasound signals to detect fluid flow within one or more vessels. The ultrasound patch assembly 10 is a self-contained unit that includes, within the housing 11, the electronics 28 that direct the piezo elements 22 to transmit the ultrasound energy, and that receive and process electronic signals from the detected echo signals. A power source 30, such as one or more batteries, antenna or other electronics for transmitting and receiving data to and from other electronic devices and/or networks, memories, speakers, etc., are included within the housing. An example of suitable internal electronics is described in U.S. Pat. Nos. 10,912,534 and 11,109,831, which are both incorporated herein in their entirety by reference thereto.

Figure 1D:
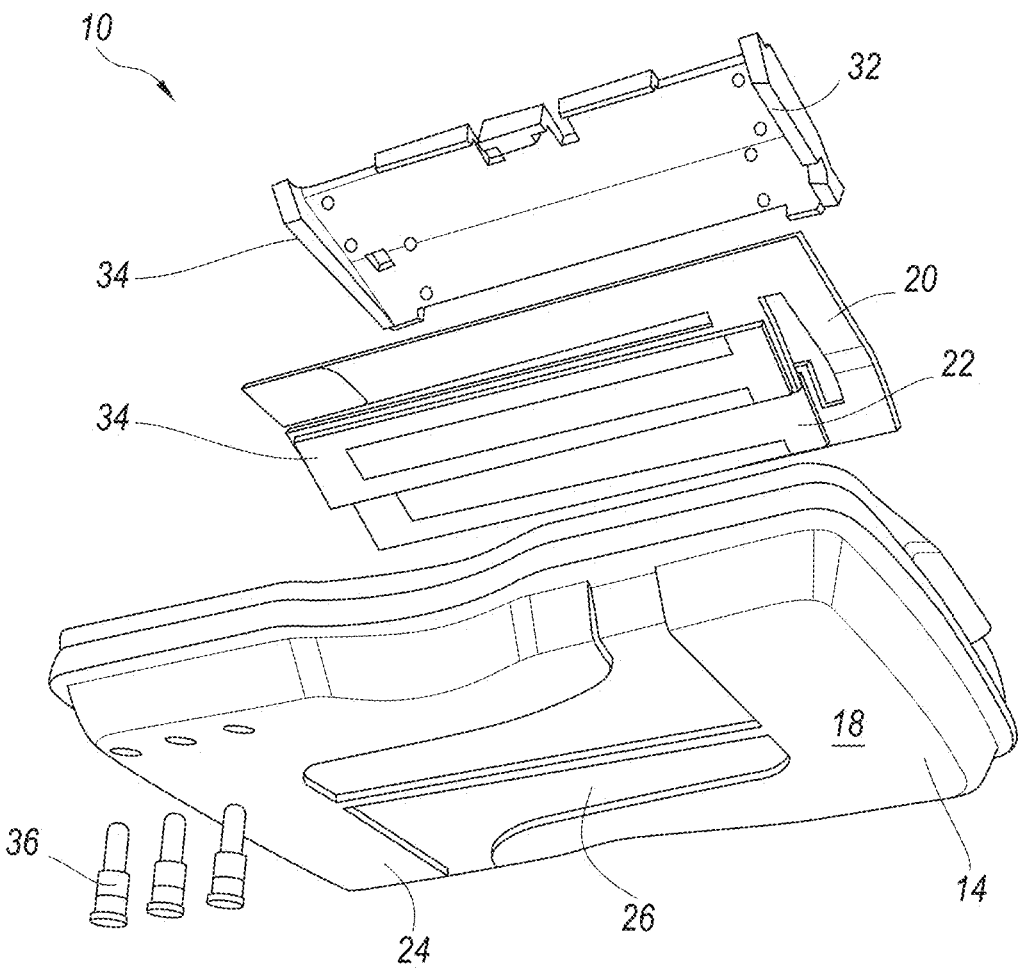
FIG. 1D is a partially exploded bottom perspective view of the ultrasound patch assembly of FIG. 1C that includes a flexible transducer assembly in accordance with embodiments of the present technology.

FIG. 1D shows a partially exploded isometric view of the bottom portion or base 14 of the ultrasound patch assembly's housing 11 in accordance with embodiments of the present technology. The housing 11 defines the interior area 16 formed at least partially by the base 14, and the interior area 16 contains a flexible transducer assembly 20 operatively coupled to the electronics also contained in the interior area 16. In the illustrated embodiment, the housing's base 14 contains a frame 32 that fixedly retains the flexible transducer assembly 20 in position, particularly during manufacture or the patch assembly 10. The frame 32 and flexible transducer element 20 together form a frame/transducer unit 34. When the frame/transducer unit 34 is positioned in the base 14, at least a portion of the outer surface of the base's bottom surface 24 provides the flat surface configured to engage the patient's skin at a selected portion of the patient's body. In some embodiments, the base 14 has a plurality of contacts 36 coupled to the electronics 28 within the housing's interior area 16. For example, the contacts 36 can provide electrical contact points for charging/recharging the ultrasound patch assembly 10, collecting data when the ultrasound patch assembly 10 is not interfacing with a patient, and/or for transmitting data to or from the self-contained patch assembly 10.

Figure 2A:
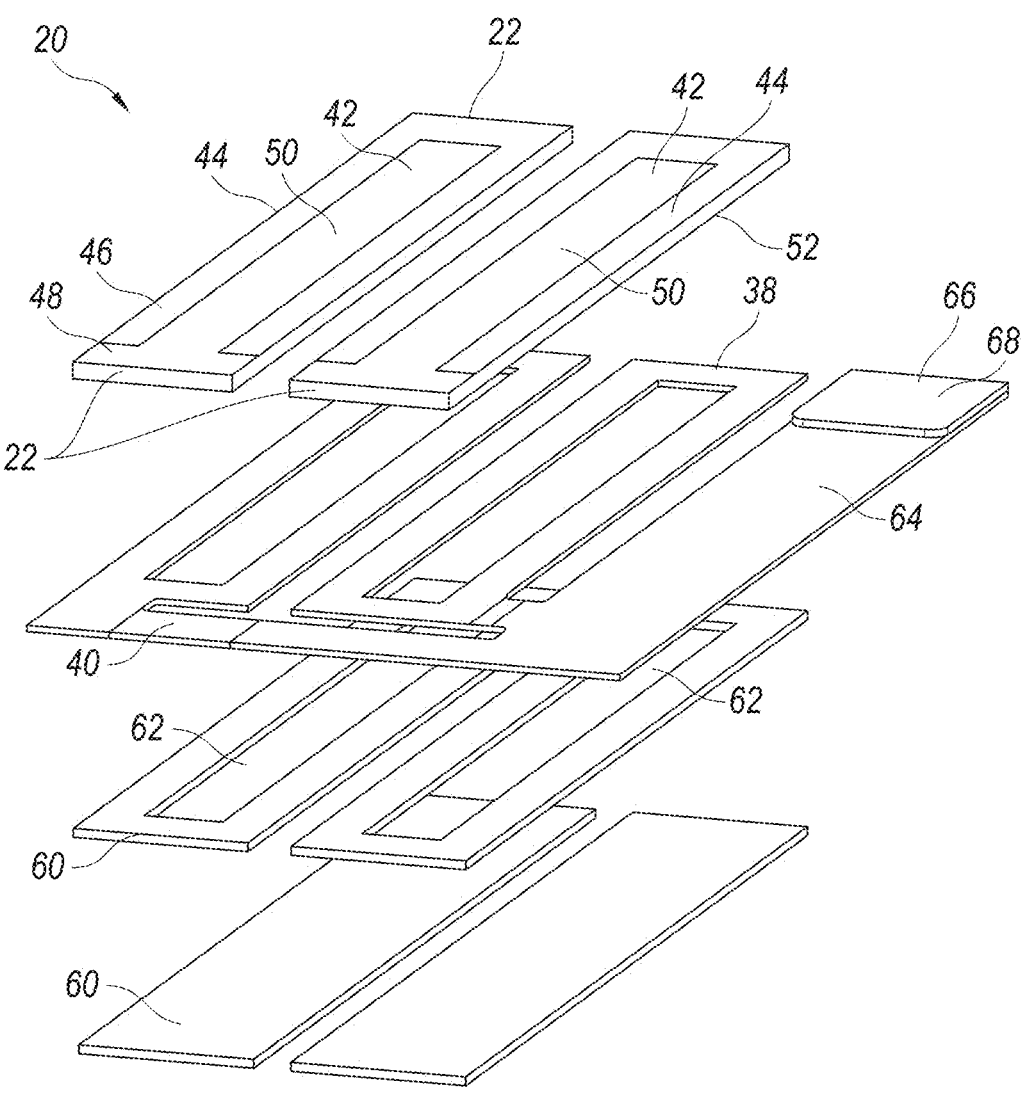
FIG. 2A is a partially exploded isometric view of a flexible transducer assembly of FIG. 1D formed in accordance with embodiments of the present technology.

FIG. 2A shows a partially exploded isometric view of the layers of a flexible transducer assembly 20 formed in a generally flat arrangement in accordance with embodiments of the present technology. Examples of flexible transducer assemblies are described in U.S. Patent Application Publication No. 2022/0000447, titled Ultrasound Patch with Integrated Flexible Transducer Assembly, which is incorporated herein in its entirety by reference thereto. The illustrated flexible transducer assembly 20 has at least a pair of piezo elements 22 mounted on a stiffened flexible (flex) layer 38, which may also be formed by a partially flexible printed circuit board (PCB) or other substrate or non-conductive support layer. As discussed in greater detail below, the flex module 38 has a hinged area 40 that allows the flexible transducer assembly 20 to selectively bend so as to position the two piezo elements 22 angularly with respect to each other and relative to the flat patient-engaging surface of the housing 11. In the illustrated embodiment, the pair of piezo elements 22 on the flexible transducer assembly 20 includes one piezo element 22 that transmits ultrasound energy, and the other piezo element 22 receives return ultrasound energy (e.g., detect echo signals). In other embodiments, the flexible transducer assembly 20 can include a plurality of pairs of piezo elements 22 patterned to form an array of elements to transmit/receive the ultrasound energy.

In some embodiments, the piezo elements 22 can be made of a rectangular sheet of Lead Zirconate Titanate (PZT) or other piezoelectric ceramic material and has length and width dimensions that define an overall surface area. In some embodiments, the length and width dimensions can be in the range of about 5 millimeters (mm) and 30 mm, respectively, although the piezo elements 22 could be made larger or smaller. In other embodiments, the width dimension can be about 4.86 mm, and the length dimension can be about 25.94 mm. An active area 42 is formed on a portion of the piezo element 22 and can have smaller length and width dimensions. In some embodiments, the length and width dimensions 110, 112 of the active area 42 can be in the range of about 24 mm and 2.5 mm, respectively. In other embodiments, the active area 42 can have different dimensions.

In the illustrated embodiment, each piezo element 22 has an inactive border 44 formed along three sides of an outer edge of the piezo element 22 around the active area 42. The border 44 is inactive because it lacks an electrode on the front surface 46. The active region within the active area 42 can achieve higher and more uniform efficiency across the entire active region as compared with a piezo element that is the size of the active area 42 that does not have the inactive border 44. In some embodiments, a smaller portion of the active area 42 can be designed as an active region.

An electrode 506 covers the active area 42 and an edge portion 48 of the border area 44. The electrode 50 continues around the edge portion 48 to a portion of the rear surface 52. Because the same, continuous electrode 50 exists on both front and rear surfaces 46, 52 of the piezo element 22, there is no voltage differential. In some embodiments, the electrode material can be approximately 10 microns thick or less. A single transmit or a single receive element can be patterned onto the active area 42 of the piezo element 22.

The configuration of the piezo element 22 with the active area 42 within the inactive border 44 helps the piezo element 22 substantially focus the beam energy along the center axis to minimize side lobe levels. Accordingly, more energy is at the center of the beam along the Doppler angle where it is desired, and less energy goes to the sides where it would contribute to clutter or noise. Therefore, the doppler signal to noise ratio (SNR) is optimized. In some embodiments, the size of the ultrasound beam can be changed or rearranged by adjusting the size and shape of the active area 42.

The piezo elements 22 are fixed to the flex module 38, so as to form sealed air gaps 54 under the active areas 42 of the piezo elements 22. The piezo elements 22 are aligned to transmit and/or receive ultrasound signals in a direction normal to a face of the respective piezo element. In some embodiments, one or both of the piezo elements 22 can be patterned to both transmit and receive ultrasound signals.

Figure 2B:
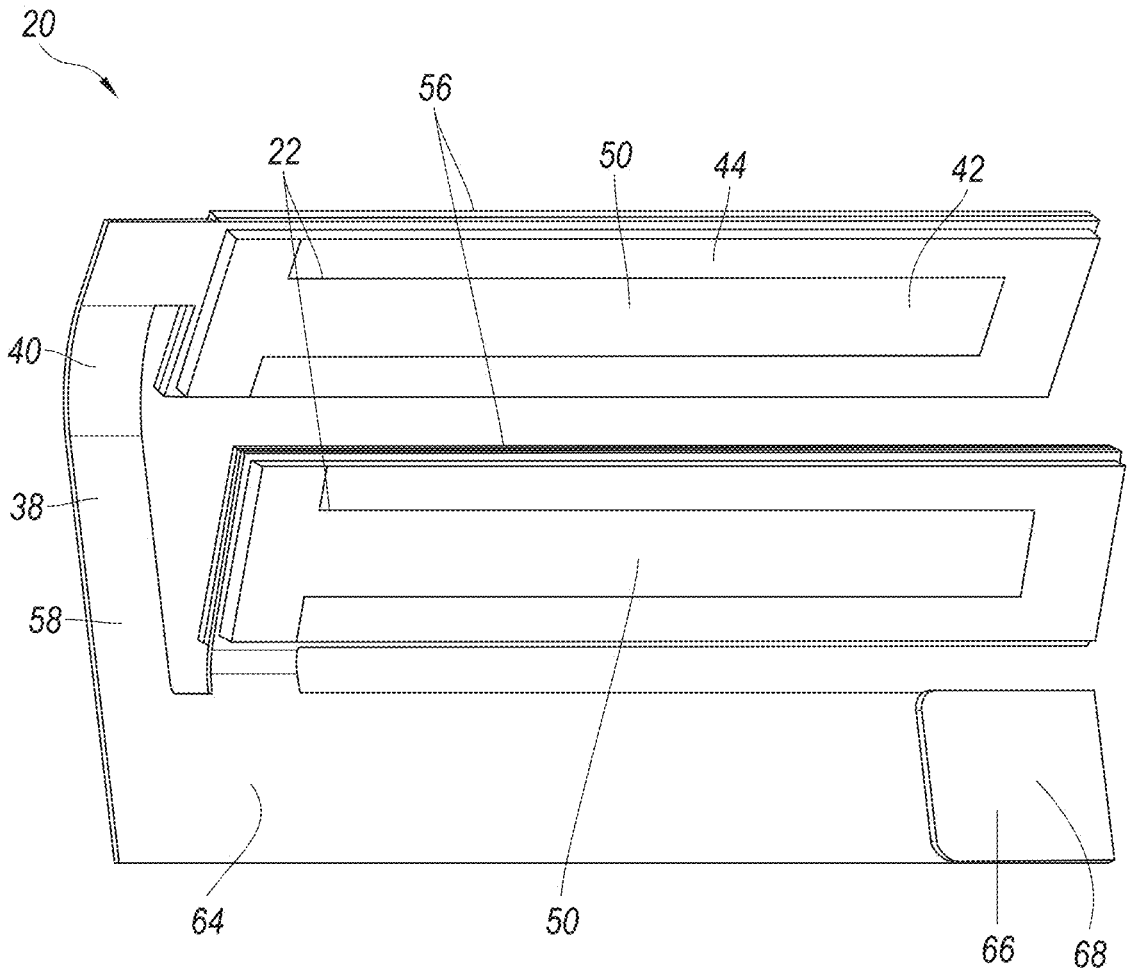
FIG. 2B is an isometric view of the flexible transducer assembly of FIG. 2A shown with transducer elements positioned at selected angular orientations.

FIG. 2B is an isometric view of the flexible transducer assembly 20 shown with the flex module 38 in a flexed or bent arrangement with the piezo elements 22 positioned at selected angular orientations. The flex module 38 can be made of material such as Polyimide and FR4 and includes embedded design circuitry and features that provide appropriate connections and convey signals between the various components and/or layers of the flexible transducer assembly 20 and other circuitry within the ultrasound patch assembly 10. At least portions of the flex module 38 can have flexibility and stiffness similar to a stiffened flex circuit and/or flexible PCB substrate, and other materials may be used to provide the desired flexibility and stiffness requirements. The flex module 38 can be fully assembled, for example, at a remote manufacturing facility and later assembled with the piezo elements 22 to form the flexible transducer assembly 20 in a flat configuration. As discussed in greater detail below, the assembled flexible transducer assembly 20 can then be selectively flexed and attached to the frame 32 to form an installation unit, and the installation unit is installed in the base 14 of the housing 11 with the piezo elements 22 in a predetermined angular orientation in a relatively quick, accurate, and easy installation process.

The flex module 38 can include a plurality of layers and thus is not limited by the description of the layers herein. Additionally, one or more of the layers discussed herein can be formed of a plurality of layers. In some embodiments, the flex module 38 can include both rigid portions 56 (e.g., FR4) and a flex portion 58 (e.g., Polyimide). The rigid portions 56 can form two rectangles 60 under the flex portion 58 that are approximately the same size as the piezo elements 22.

The flex portion 58 can be attached to portions of the rigid portions 56 and connect to the hinged area 40 to join the two rectangles 60 of the rigid portions 56. The flex portion 58 extends along edge portions of the rectangles 60 that correspond with the borders of the piezo elements 22. The area shown that corresponds to the air gaps 62 (FIG. 2A) is an exposed area of the rigid portion 56 that seals the air backing under the active area 42 and provides mechanical stability to the regions under the piezo elements 22.

The flex portion 58 forms a flexible "tail" 64 that extends away from the piezo elements 22. The tail 64 leads to a stiffened tab 66 that can include parts of the rigid portion 56 and the flex portion 58. A board-to-board connector 68 is shown on the top surface of the stiffened tab 66, although there are other possible connectors that could be used and the position of the connector 68 is not limited as shown. The tab 66 is stiffened to facilitate coupling the connector 68 with other appropriate connections to electronics within the patch transducer 10. The tail 64 is not limited to the shape and configuration shown. In some embodiments, the rigid portion 56 can be included in areas of the tail 64 other than the stiffened tab 66. Electrical contacts can be patterned onto a front surface of the flex portion 58. This allows electrical connection to the piezo elements 22 to be achieved. The electrical contacts can be configured as signal electrodes and ground electrodes. In some embodiments, the signal and ground configurations can be swapped.

Figure 3A:
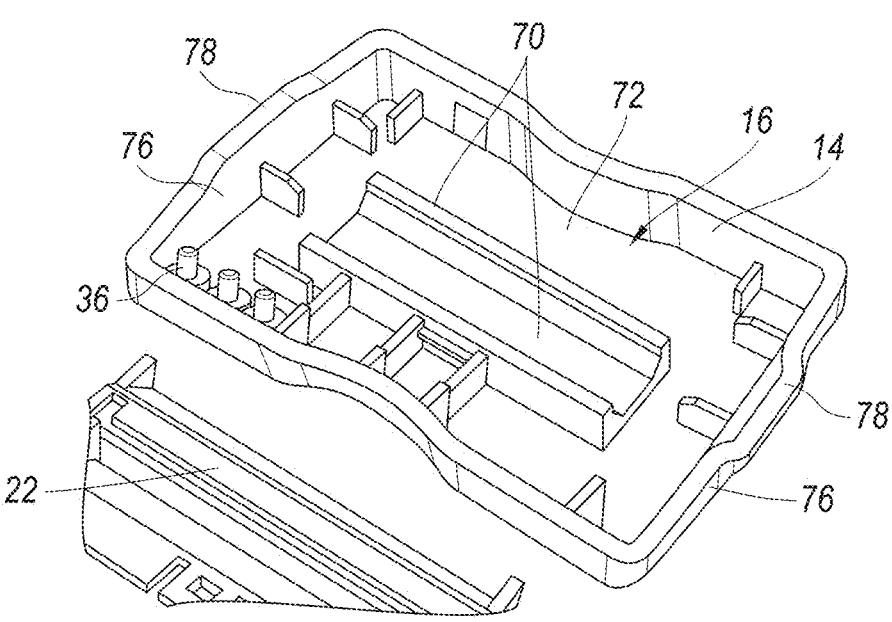
FIG. 3A is an isometric view of an interior area of a base of the ultrasound patch assembly formed in accordance with embodiments of the present technology.
Figure 3B:
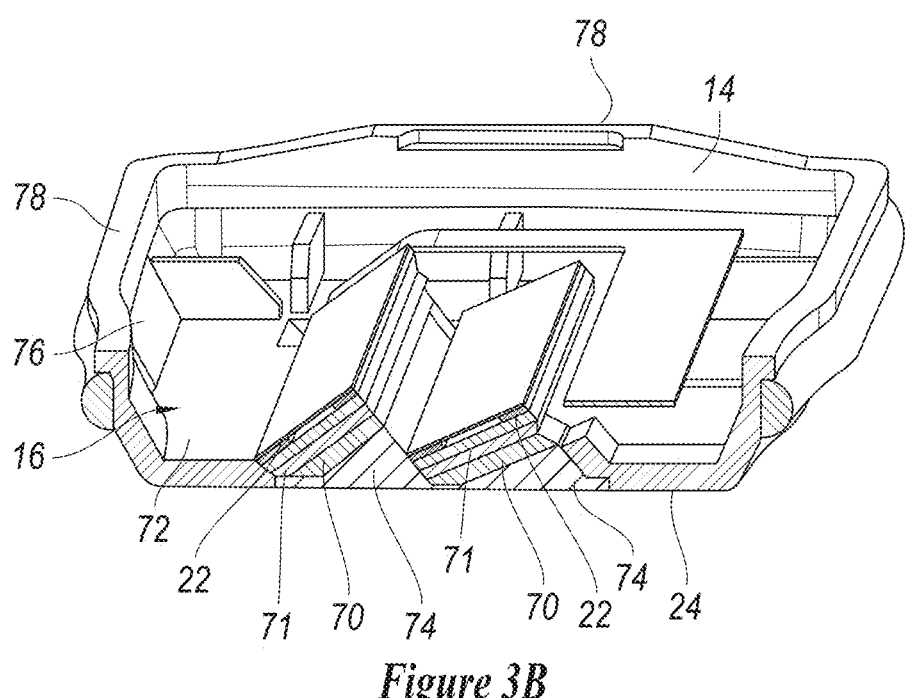
FIG. 3B is a cross-sectional view of the base of FIG. 3A with the flexible transducer assembly secured in position within the base.

FIG. 3A is a top isometric view of the base 14 showing at least a portion of the interior area 16 of the housing 11, and FIG. 3B is a cross-sectional view of the base 14 with the flexible transducer assembly 20 secured in position within the base 14. The base 14 has a pair of angled support members 70 projecting from the bottom 72 of the base 14. The angled support members 70 are positioned at selected angles relative to the base's flat bottom surface 24 that faces and engages patient's skin. As seen in FIG. 3B, the angled support members 70 each provide a flat, rigid mounting surface to which the piezo elements 22 are fixedly secured to precisely retain the piezo elements 22 at selected angular orientations relative to the base's bottom surface 24. In the illustrated embodiment, the angled support members 70 are integrally formed as part of the base 14, and the angled support members 70 are positioned at different angles as desired to provide a selected intersection depth of the ultrasound beams during use of the ultrasound patch assembly 10 (FIG. 1A).

During manufacture of the ultrasound patch assembly 10, the flexible transducer assembly 20 is position in the base 14 with the assembly bending at the flex portion 58, so the rigid portions 56 and associated piezo elements 22 are oriented at selected angles to match the different angular orientations of the angled support members 70 (FIG. 3B). In the illustrated embodiment, the piezo elements 22 are affixed to the angled support members 70 by, for example, a non-conductive epoxy 71 or other suitable adhesive that prevents any relative movement of the piezo elements 22 and the angled support members 70 once the flexible transducer assembly 20 is mounted in the base 14. This arrangement with the angled support members in the base defining the orientation of the piezo elements 22 allows the piezo elements 22 to be positioned in relatively shallow angles while minimizing the structures and height needed to accommodate the components in the housing. This arrangement can substantively decrease the overall height and footprint of the ultrasound patch assembly 10.

By defining the angular relationship of the support members 70 relative to each other, the imaging depth of the flexible transducer assembly 20 can be changed. For example, two bases 14 can have substantially identical constructions, except for the angle between the support members 70. Each of the two bases 14, however, could easily and quickly receive the same flex module 38 during assembly. This allows the flex module 38 to be manufactured, for example, in a flat arrangement, and then flexed during assembly to position the respective piezo elements 22 at the angular orientation defined by the support members 70 onto which the flex module is adhered or otherwise affixed. Accordingly, the support members 70 of a first base may be set in a first angular arrangement to achieve, for example, a two-centimeter (cm) intersection depth of the ultrasound beams, and the support members 70 of a second base may be set at a second angular arrangement to achieve, for example, a four cm intersection depth. Other bases 14 could be configured to support piezo elements 22 at other angles to achieve other intersection depths.

As seen in FIGS. 3B, the base 14 can include one or more beam lenses 74, such as a soft lens material or other selected beam directing features positioned on the bottom of the base below the angled support members 70 opposite the respective piezo elements 22. The beam lenses 74 can be a soft plastic material with a different hardness than the angled support members 70 and configured to direct the ultrasonic beams from and to the piezo elements 22 that are not normal to the respective planes of the piezo elements 22, depending upon the desired intersection depth of the ultrasound beams for the ultrasound patch assembly 10. This arrangement can allow the angled support members 70 and the mounted piezo elements 22 to be at even shallower angles to further reduce the height of the ultrasound patch assembly 10, while still maintaining the desired beam intersection depth via use of the lenses 74 positioned at the skin contacting portion of the base 14. Further, with the piezo elements 22 and lenses 74 (when used) positioned very close to the inner surface of the flat skin contacting portion 26 and thus also the target area of the patient, lower power is needed for driving the piezo elements during the ultrasound process.

As seen in FIG. 3A, the base 14 has sidewalls 76 that protrude upwardly from the bottom 72 of the base 14. The upper edges 78 of the sidewalls 76 can have one or more protrusion, recess, and/or other interlocking members to facilitate mating the base 14 and the housing's top portion 12 (FIG. 1).

Figure 3C:
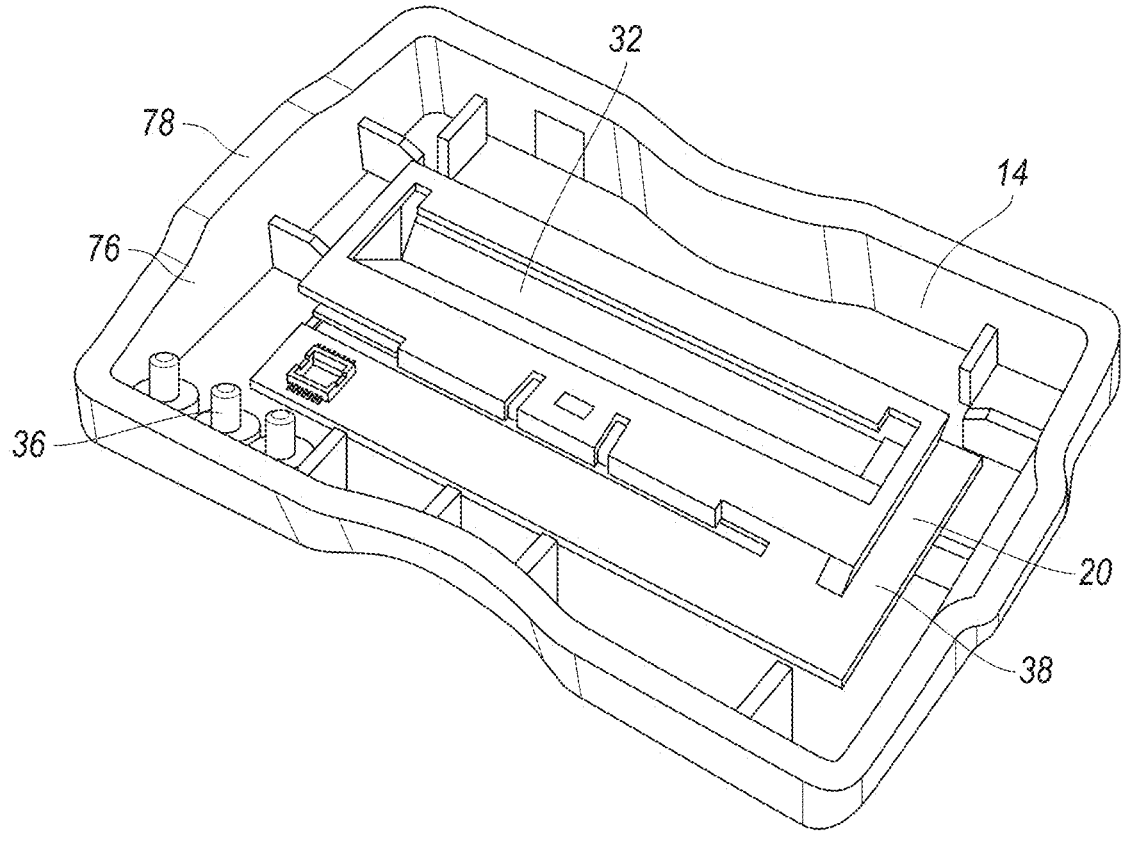
FIG. 3C is an isometric view of the base of FIG. 3A mated with the transducer frame and flexible transducer assembly in accordance with embodiments of the present technology.
Figure 4A:
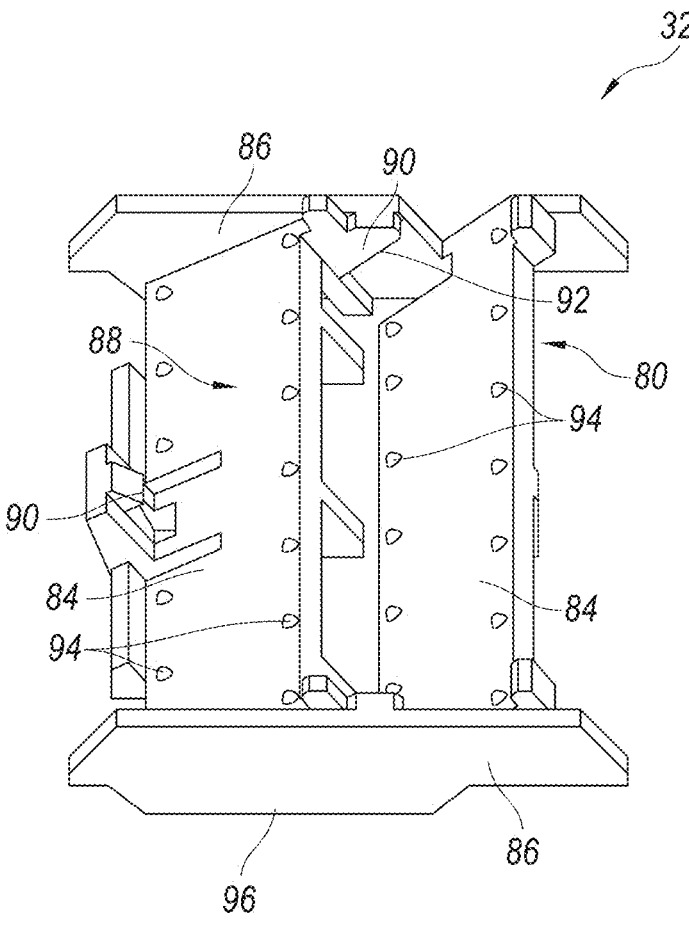
FIG. 4A is a top isometric view of the transducer frame of FIG. 1D showing a plurality of crush points positioned on the frame surface in accordance with embodiments of the present technology.
Figure 4B:
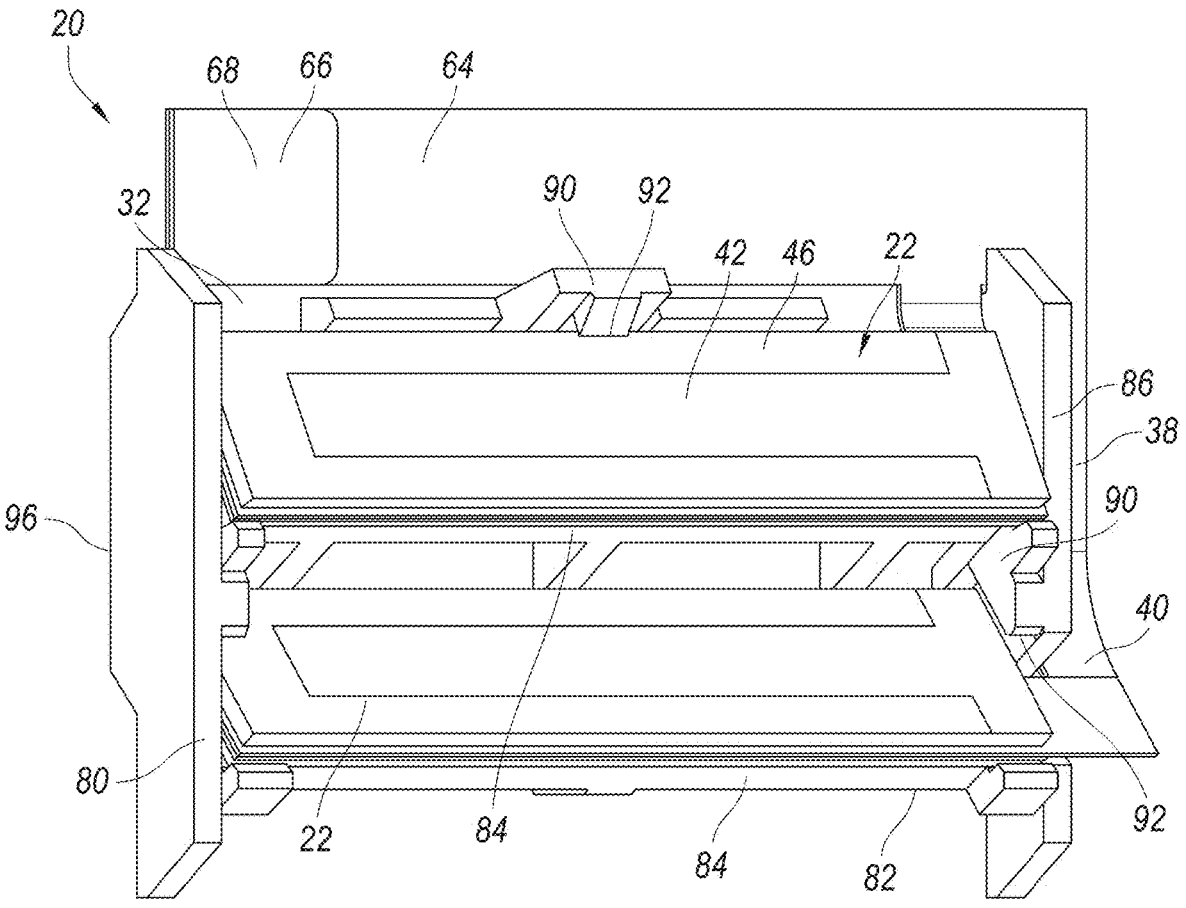
FIG. 4B is a bottom isometric view of the flexible transducer assembly of FIG. 2B supported in the transducer frame of FIG. 4A.
Figure 4C:
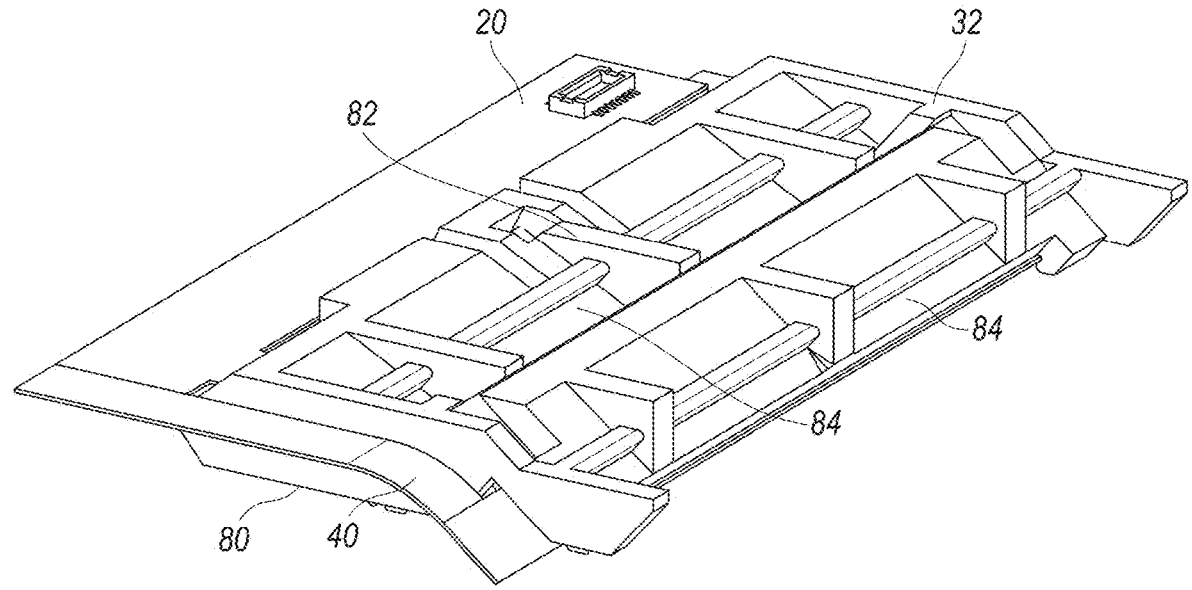
FIG. 4C is a top isometric view of the transducer frame and the flexible transducer assembly of FIG. 2B before installation into the base.

As indicated above, the housing's base 14 contains the frame 32 that sandwiches the flexible transducer assembly 20 in position on the angled support members 70, as seen in FIG. 3C. In the illustrated embodiment, the flexible transducer assembly 20 is attached to the frame 32 during the manufacturing process before the components are positioned in the base and against the angled support members 70. FIG. 4A-4C are isometric views of the transducer frame 32 configured to support and hold the flexible transducer assembly 20 of FIG. 2B generally in a desired angular orientation. FIGS. 4A and 4B are bottom views of the frame's lower portion 302 that receives and holds the flexible transducer assembly 20 (FIG. 4B) in the angular orientation defined by the structure of the frame 32. FIG. 4C primarily shows a top side 82 of the frame 32 that faces upwardly away from the base 14 (FIG. 3C). The transducer frame 32 can be made of rigid plastic or other substantially rigid, non-conductive material. The transducer frame 32 is configured for easy and accurate assembly of the flexible transducer assembly 20 into the base 14 and held securely against the angled support members 70 (FIG. 3B) as the piezo elements 22 are being bonded to the angled support members 70.

Referring to FIG. 4A, the transducer frame 32 of the illustrated example includes a pair of spaced apart support panels 84 that engage the flex module 38. The support panels 84 are each oriented at specific angles that match the angular orientation of the angled support members 70 in the base 14 (FIG. 3B). Accordingly, the frame's support panels 84 work to position and retain the piezo elements 22 of the flexible transducer assembly 20 at the desired angular orientations for precise positioning of the piezo elements 22 in the base 14.

In some embodiments, each frame 32 is matched with a base 14 so that the angular orientation of the frame's support panels 84 substantially matches the angular orientation of the base's angled support members 70. This allows the piezo elements 22 to be firmly sandwiched between the frame 32 and the angled support members 70. The frame also acts to uniformly press the piezo elements 22 against the angled support members 70, such as when the piezo elements are being adhered in place with the epoxy during manufacturing. This matching of a frame 32 with a base 14 to have the same angular orientations of the frame's support panels 84 and the base's angled support members 70 allows for quick and easy assembly of an ultrasound patch assembly 10 with a predetermined imaging depth.

As seen in FIGS. 4A and 4B, support panels 84 extend between sidewalls 86 of the frame 32 to form a receiving area 88 for the flexible transducer assembly 20. The illustrated frame 32 has integral retention features 90 with lower engagement surfaces 92 to securely capture the flexible transducer assembly 20 in place on the frame 32 and hold the flexible transducer assembly 20, so as to provide a frame/transducer unit 34 that can be installed into the base 14, as discussed in greater detail below.

The frame 32 is also configured to precisely align the piezo elements 22 of the flexible transducer assembly 20 on the frame 32. Accordingly, during the manufacturing process, the flexible transducer assembly 20 is mounted and aligned on the frame 32, which matches the selected base as discussed above. Epoxy or other selected adhesive can be applied to the piezo elements 22 and/or to the angled support members 70. The frame/transducer unit 34 can be easily and accurately pressed into position into the base 14, so as to firmly position and precisely align the piezo elements 22 onto the base's angled support members 70 as the epoxy cures to permanently retain the piezo elements in position on the base.

In the embodiment shown in FIG. 4A, the transducer frame 32 has a plurality of sacrificial crush points 94 projecting from support panels 84. The crush points 94 are configured to engage the flexible transducer assembly 20 adjacent to the piezo elements 22 (FIG. 4B). The crush points 94 protruding from the support panels 84 provide an alignment surface against which the flexible transducer assembly 20 is firmly pressed against to register and ensure that the flexible transducer assembly 20 is in the correct and precise location relative to the frame 32. In certain embodiments, the crush points 94 can interface with the rigid portion 56 behind or next to the piezo elements 22. In some embodiments, a plurality of frames 300 have the crush points 94 in substantially the same locations even though the angular orientation of the support panels 84 may be different in different frames 32. The crush points 94 can be a stiff but deformable material to press firmly against the flexible transducer assembly 20 as the frame/transducer unit 34 is moved into position in the base against the angled support members 70 (FIG. 3A).

The base 14 is configured to closely receive the frame 32 adjacent to the angled support members 70. During assembly of some embodiments, after a thin layer of epoxy 71 has been applied to the piezo elements 22 and or the respective angled support members 70, the frame/transducer unit 34 is moved into position in the base with the piezo elements 22 pressing against angled support members 70. The top side 82 of the frame 32 (FIG. 4C) is configured so a press tool or the like can press against the frame 32, thereby pressing and holding the piezo elements 22 in precise position against the base's angled support members 70. The pressures applied by the press tool against the top side 82 of the frame 32 is such that the crush points 94 apply uniform pressure against to the flexible transducer assembly 20 for exact positioning of the piezo elements 22 in the base 14. In the illustrated embodiments, the crush points 94 are shaped and sized so that, during assembly, they will deform (e.g., plastic deformation) to concentrate the pressure against the flexible transducer assembly 20 until the epoxy is sufficiently cured to hold the flexible transducer assembly 20 in position on the base's support members 70.

Referring again to FIG. 3C, this figure illustrates the base 14 mated with the frame/transducer unit 34 in accordance with embodiments of the present technology. The manufacturing tolerances for the distance and angles in the support and alignment members of the base 14 and the frame 32 are strictly controlled to provide the precision needed to achieve the directionality of the piezo elements 22. Each transducer frame 32, regardless of the angular orientation of the frame's support panels 304, is configured to mate with the matching base 14, providing the ability to manufacture the ultrasound patch assemblies 10 that can be used in different scanning applications while using the same manufacturing processes, the same base 14, and the same matching flexible transducer assembly 20. Accordingly, the base 14 has common receiving features configured with a common configuration that quickly, easily, and accurately accepts sidewalls of one frame 32 for precise positioning of the frame's support panels and the piezo elements against the base's angled support members. This simple and precise process facilitates quick assembly and can eliminate the need for costly trained labor.

Figure 5:
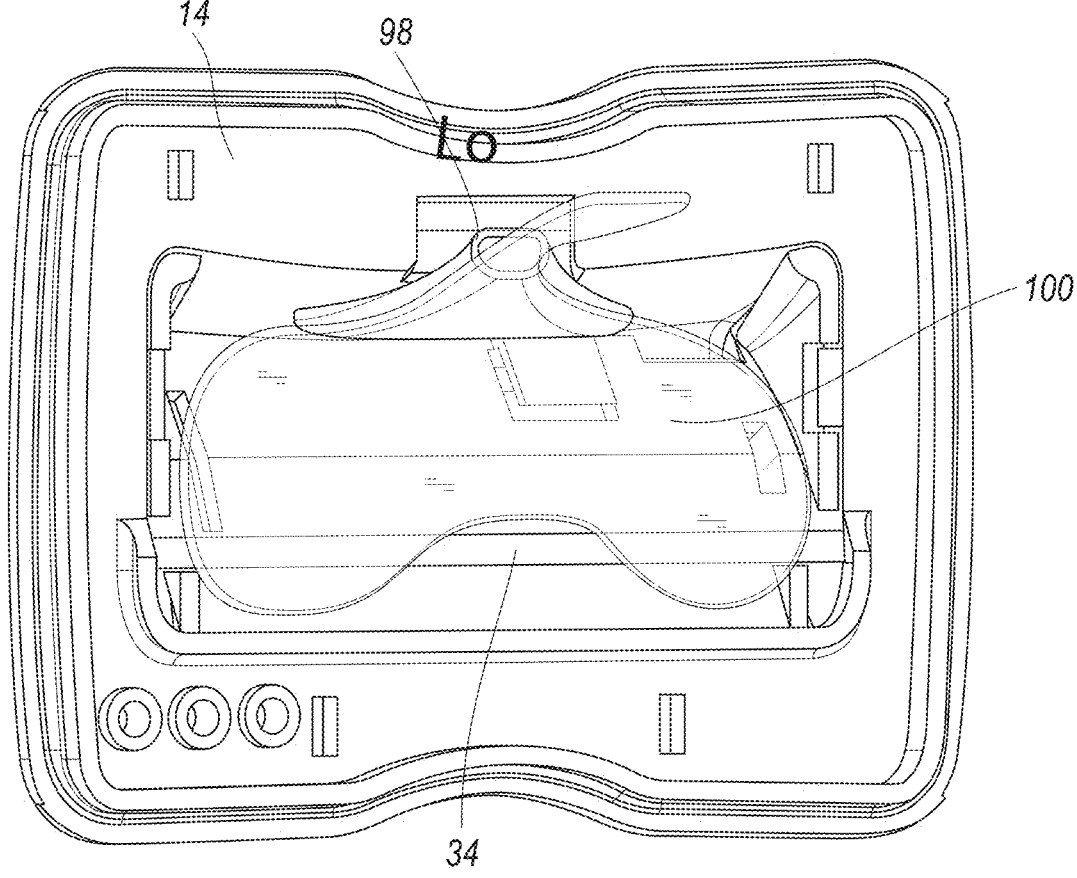
FIG. 5 is an isometric view of the base, transducer frame, and flexible transducer assembly of FIG. 3E shown during an intermediate portion of a geometry guided epoxy potting process in accordance with embodiments of the present technology.

In some embodiments, the base 14 can be configured to allow for guided epoxy potting of the flexible transducer assembly 20 in the base 14 of ultrasound patch assembly 10. For example, as illustrated in FIG. 5, the base can have a guide hole 98 and one or more potting channels adjacent to the area that receives the frame/transducer unit 34. The guide hole 98 and channels can be molded into the portion of the base 14 that receives the frame/transducer unit 34.

After the frame/transducer unit 34 has been snapped into the base 14 and the piezo elements positioned adjacent to the angled support members 70, potting epoxy 100 can be deposited or provided (e.g., such as through a nozzle of a syringe, a deposition gun, etc.) through the guide hole 98 or directly into the potting channels that funnel the epoxy 100 to the area between the piezo elements 22 and the angled support members 70. Epoxy 100 or other potting material, shown in shadow on FIG. 3H, can also be introduced directed into the base area to encapsulate the frame/transducer unit 34 affixed within the base 14. The epoxy 100 can be selected based on its acoustic properties, such as speed of sound and attenuation, to ensure that the angle of the beam as it exits/enters the base 14 is known and does not change.

In some embodiments, the epoxy 100 can be provided through the guide hole 98 and flows about the piezo elements 22. The controlled manner in which the epoxy 100 is applied can flood the inside of the base 14 uniformly and cover at least the front surfaces of the piezo elements 22 of the flexible transducer assembly 20. The controlled application of epoxy 100 can also allow for air bubbles to rise and escape from the assembly.

In some embodiments, the angled support members 70 are shaped and oriented to set a transmit/receive direction of the piezo elements 22 in a range from about 20-60 degrees with respect to the direction of flow in a vessel when the ultrasound patch assembly 10 is in use on a patient. In some cases, the preferred angle is in the range of approximately 25-35 degrees, and even more specifically approximately 30 degrees depending on the desired intersection depth of the ultrasound beams depth.

Figure 6A:
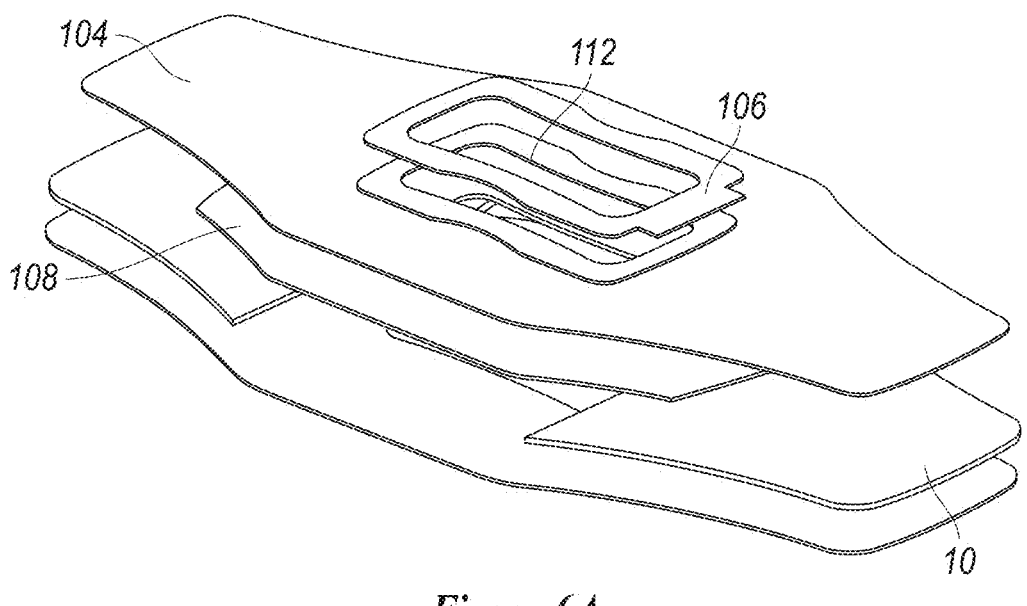
FIGS. 6A and 6B are partially exploded isometric and side views, respectively, of the ultrasound patch assembly FIG. 1A shown attached to an adhesive layer for use on a human body in accordance with embodiments of the present technology.
Figure 6B:
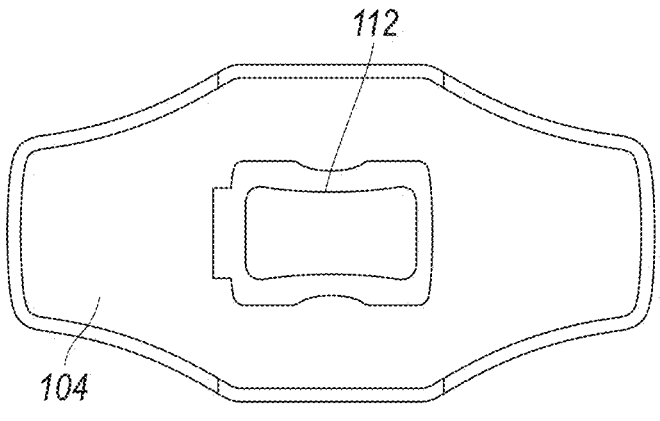

An embodiment of the ultrasound patch assembly 10 can be attached to an adhesive for use on a human body in accordance with embodiments discussed above. In some embodiments, such as in FIGS. 6A and 6B, an adhesive layer 104 can be used to attach at least part of the skin contacting portion 26 to the skin of a patient, while an acoustic coupling material 106 is used between the skin of the patient and the surface of the base 14. In other embodiments, the adhesive 58 can be an acrylate adhesive and form a wing-like shape configured to firmly hold the ultrasound patch assembly 10 on the patient in a hands-free arrangement. The acoustic coupling material 106 can include a dual material hydrogel 108, which will prevent soiling of the adhesive after initial placement of the skin contacting portion 26 to the skin of a patient. In certain embodiments, the dual material hydrogel 108 can be an ultrasound hydrogel or an acoustic hydrogel. Additionally, the acoustic coupling material 106 can include a dual liner 110 (e.g., kraft paper), which is placed under the hydrogel 108. In still further embodiments the adhesive 104 can have an opening 112 to allow the ultrasound patch assembly 10 to attach to the adhesive. The opening 112 can go around the ultrasound patch assembly 10, allowing the patch transducer 10 to be used with multiple adhesive layers 104.

Further, in other embodiments, a fastener or adhesive can be used over at least a portion of the top side of the patch transducer 10 to further secure it to the patient. This can provide the advantage of preventing undesirable decoupling, movement, or migration of the patch transducer 10 away from the desired imaging location. In some cases, the patch transducer 10 can move or migrate on the patient over time or when the patient moves or is moved, and thus may image a different location of the patient or become decoupled from the patient. An adhesive can be made of tape or bandage materials or can be a film dressing such as Tegaderm©, which is produced by 3M©. An adhesive can provide a force normal to the skin of the patient to retain the patch transducer 10 in a fixed position relative to the patient's skin. Some adhesives can provide a compressive force to hold the patch transducer 10 in the fixed position, thus retaining the patch transducer 10 in proper alignment (e.g., vertical, angular, lateral, etc.). In some cases, some adhesives can interface with the skin of the patient and provide a pulling force that securely pulls the skin proximate the patch transducer 10 toward the patch transducer 10. Other fastening mechanisms such as a strap may be used, such as those disclosed in U.S. patent application Ser. No. 16/377,028, filed Apr. 5, 2019, (published as U.S. 2020-0022670 A1).

In some cases, a hydrophobic or foam adhesive ring can be used attached to the skin contacting portion 26. The hydrophobic adhesive ring can provide a barrier to prevent the seepage of acoustic coupling beyond the outer edges of the patch transducer 10. The hydrophobic adhesive ring can also attach the patch transducer 10 to the patient or can be used together with another fastener/adhesive. In other embodiments, a well or depression (not shown) can be formed in the skin contacting portion 26 between the bottom side 12 and outer edges of the patch transducer 10 and/or adhesive/fastener that interfaces with the skin contacting portion 26 to collect acoustic coupling medium that may seep beyond the outer surface of the base 14.

An advantage of the proposed embodiment is that the ultrasound patch assembly 10 can be fully assembled inside the base 14. In other embodiments, some of the components can be fixed inside the top shell 12 before the top shell 12 and base 14 are mated together. This facilitates a systematic and reproducible manufacturing process. Other components, interconnects, and structures designed to provide the desired functionality and secure the components (e.g., circuit board (s), battery, electronics, memories, antenna, speaker, etc.) that generate the ultrasound signals, detect a Doppler shift in a vessel and produce an output indicative of the Doppler shift, as well as transmit the signal data to a remote device can be held within the top shell 12 and/or base 14. The remote device or base unit (e.g., dedicated ultrasound machine, computer and/or handheld device such as a smart phone or tablet that has an application installed thereon for communicating with the patch assembly 10) can transmit and receive information to/from the patch assembly 10.

In some embodiments, the patch assembly 10 can be used by a single patient. In other embodiments, the patch assembly 10 can be refurbish-able (e.g., facilitate an upgrade, repair, etc.) and/or repurposed for use with multiple patients. Accordingly, the waterproofing can allow for the sterilization of the patch assembly 10 when using hydrogen peroxide or other appropriate cleaning chemicals, and/or ultrasonically cleaning in a liquid solution.

Implementing an ultrasound patch assembly 10 with a flat bottom side 12 of the present technology improves the physiological signal being emitted from the blood of the patient's jugular vein. The jugular vein is a collapsible vein, thus any additional and unnecessary force on the vein can constrict blood flow, which can result in a poor physiological signal. The flat bottom side will also remove the extra pressure on the skin of the human subject, which will allow the blood to move more freely and collect physiological data from a richer signal.

I claim:

1. An ultrasound patch assembly configured for use on the skin of a patient to detect fluid flow in a vessel in the patient, comprising:

two piezoelectric (piezo) elements configured to transmit ultrasonic energy and detect echo signals, each piezo element having a central active area;

a flex module comprising first and second support portions connected to a respective one of the two piezo elements, the flex module further comprising a hinged portion coupled to the first and second support portions and configured to allow the first and second support portions to be positioned angularly relative to each other, the flex module further comprising a first alignment portion;

a pair of rigid backing structures each fixedly attached to a respective one of the piezo elements, each rigid backing structure having a blind opening in alignment with the central active area of the respective piezo element, wherein the piezo elements, the flex module, and the rigid backing structures form a transducer assembly;

electronics in communication with the piezo elements through the flex module, the electronics configured to direct the piezo elements to transmit the ultrasonic energy, the electronics further configured to process the detected echo signals;

a transducer frame comprising first and second surfaces that receive the first and second support portions of the flex module with the rigid backing structure sandwiched between the respective first and second surfaces and the respective rigid backing structure, the first and second surfaces each having a plurality of deformable protrusions engaging the respective rigid backing structures and positioning the transducer assembly on the transducer frame with the piezo elements in a selected position relative to the first and second surface, the first and second surfaces having an angular arrangement to position the two piezo elements at one of a plurality of angles relative to each other and wherein the transducer frame have integral retention features with engagement surfaces engaging perimeter portions of the piezo elements and holding the transducer assembly in position on the first and second surfaces of the transducer frame; and a housing that encloses the electronics and the transducer frame within an interior area, the housing including a top surface opposite a bottom surface, the top surface configured to face away from the skin of the patient and the bottom surface configured to face toward the skin of the patient during use with the patient, the housing having a pair of angled support members oriented at angles relative to the bottom surface, the housing having a receiving area that receives and retains the transducer frame, with the piezo elements positioned against the pair of angled support members at the angles with the piezo elements and at least a portion of the flex module are sandwiched between the angled support members and the frame at the angles to transmit the ultrasonic energy toward the bottom surface and away from the top surface.

2. The ultrasound patch assembly of claim 1 wherein active areas of the two piezo elements comprise less than an entire surface area of each of the two piezo elements.

3. The ultrasound patch assembly of claim 1 wherein portions of the two piezo elements and the flex module are electrically interconnected.

4. The ultrasound patch assembly of claim 3 wherein the two piezo elements are positioned over the flex module and pushed together, creating a contact that electrically interconnects the two piezo elements and the flex module.

5. The ultrasound patch assembly of claim 3 wherein an epoxy is applied on a surface of the flex module to maintain a bond when the two piezo elements and the flex module are electrically interconnected.

6. The ultrasound patch assembly of claim 1 wherein the two piezo elements each have a length and a width defining surface areas of the two piezo elements, the two piezo elements configured to have acoustically active areas that are a subset of the surface areas, wherein the acoustically active areas are surrounded by acoustically inactive areas that are positioned along outer edges of the surface areas, the flex module further comprising:

electrodes positioned between the acoustically inactive areas of the two piezo elements and the first and second support portions; and pressure contact to electrically interconnect the two piezo elements and the electrodes.

7. The ultrasound patch assembly of claim 1 wherein the deformable protrusions are crush points positioned on the first and second surfaces.

8. The ultrasound patch assembly of claim 1 wherein the housing includes a top shell and a base that are configured to be snapped together.

9. The ultrasound patch assembly of claim 1 wherein the bottom surface of the housing further comprises a flat central portion to form a cavity, the transducer frame being held partially within the cavity of the housing.

10. An ultrasound patch assembly configured for use on the skin of a patient to detect fluid flow in a vessel in the patient, comprising:

piezoelectric (piezo) elements configured to transmit ultrasonic energy and detect echo signals, the piezo elements having front and rear surfaces;

a flex module comprising:

first and second support portions and a hinged portion coupled to the first and second support portions to allow the first and second support portions to be positioned angularly relative to each other;

electrodes positioned on the first and second support portions; and a pair of rigid backing structures each fixedly attached to a respective one of the piezo elements, each rigid backing structure having a blind opening in alignment with a central active area of the respective piezo element, wherein the piezo elements, the flex module, and the rigid backing structures form a transducer assembly;

pressure contact to electrically interconnect the rear surfaces of associated ones of the piezo elements and the electrodes, wherein a non-conductive epoxy forms a bond between the electrically interconnected piezo elements and the electrodes;

a transducer frame made of a rigid material and having first and second surfaces and sidewalls that extend outwardly from opposite ends of the first and second surfaces, the sidewalls and first and second surfaces forming a receiving area for the first and second piezo elements, the first and second surfaces receive the first and second support portions of the flex module with the rigid backing structure sandwiched between the respective first and second surfaces and the respective rigid backing structure, the first and second surfaces each having a plurality of deformable protrusions engaging the respective rigid backing structures and positioning the transducer assembly on the transducer frame with the piezo elements in a selected position relative to the first and second surface, the first and second surfaces having an angular arrangement to position the front surfaces of the first and second piezo elements at less than 180 degrees with respect to each other, at least one of the sidewalls including a retention feature protruding from the sidewall into the receiving area proximate the front surface of at least one of the first and second piezo elements; and a housing comprising:

a top shell that has a top surface configured to face away from the skin of the patient; and a base that has a bottom surface opposite the top surface of the top shell, the bottom surface configured to face toward the skin of the patient during use with the patient, the base having a pair of angled support members oriented at angles relative to the bottom surface, the housing having a receiving area that receives and retains the transducer frame with the piezo elements positioned against the pair of angled support members at the angles with the piezo elements and at least a portion of the flex module are sandwiched between the angled support members and the transducer frame at the angles.

11. The ultrasound patch assembly of claim 10 wherein the bottom surface forms a flat surface corresponding to the cavity that includes a flat face, the piezo elements configured to transmit the ultrasound energy and detect the echo signals through the flat face.

12. The ultrasound patch assembly of claim 10 wherein the deformable protrusions are a plurality of crush points positioned on the first and second surfaces.

13. The ultrasound patch assembly of claim 10 wherein the angular arrangement of the first and second surfaces of the transducer frame is determined based on an imaging depth.

14. The ultrasound patch assembly of claim 10 wherein the transducer frame includes sidewalls that extend outwardly from the first and second surfaces, the sidewalls and first and second surfaces forming a receiving area for the first and second support portions and the piezo elements.

15. The ultrasound patch assembly of claim 10, wherein each rigid backing structures comprises a first plate and a second plate affixed to the first plate, wherein the second plate has an aperture therein aligned with the active area of the piezo element, with the second plate fixedly sandwiched between the first plate and the piezo element to form the blind opening.

16. The ultrasound patch assembly of claim 10, wherein the receiving area is made of a soft material.

17. The ultrasound patch assembly of claim 1 wherein the piezo elements are fixedly bonded to the angled support members of the housing.

18. The ultrasound patch assembly of claim 1 wherein the plurality of deformable protrusions are a plurality of sacrificial crush points configured to deform and align the piezo elements when the transducer assembly is mounted against the first and second surfaces of the housing.

19. The ultrasound patch assembly of claim 1 wherein transducer assembly is configured to snap into engagement with the retention features with the piezo elements aligned with the first and second surfaces of the housing.

20. The ultrasound patch assembly of claim 1 wherein transducer assembly is potted with epoxy in the housing.

* * * * *